United States Patent [19]
Corzani

[11] Patent Number: 5,969,025
[45] Date of Patent: *Oct. 19, 1999

[54] WATER-BASED ADHESIVE COMPOSITION WITH BOND RETENTION IN THE PRESENCE OF WATER

[75] Inventor: Italo Corzani, Chieti, Italy

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/549,758

[22] PCT Filed: May 16, 1994

[86] PCT No.: PCT/EP94/01576

§ 371 Date: Feb. 29, 1996

§ 102(e) Date: Feb. 29, 1996

[87] PCT Pub. No.: WO94/26834

PCT Pub. Date: Nov. 24, 1994

[30] Foreign Application Priority Data

May 17, 1993 [IT] Italy .................................. TO93A0338

[51] Int. Cl.$^6$ ............................ C08L 93/04; C08L 33/06; C09J 133/06; C09J 125/04
[52] U.S. Cl. ........................ 524/272; 524/274; 525/143; 525/149; 525/218; 525/221; 525/227; 156/327; 156/334
[58] Field of Search ...................................... 524/272, 274; 525/143, 149, 218, 221, 227; 156/327, 334

[56] References Cited

U.S. PATENT DOCUMENTS 4,438,232  3/1984  Lee ........................................... 525/221
4,714,728  12/1987  Graham et al. .......................... 524/272
4,767,813  8/1988  Evitt ........................................ 524/272
5,196,468  3/1993  Schwerzel et al. ..................... 524/272
5,284,891  2/1994  Wouters et al. ......................... 525/221

FOREIGN PATENT DOCUMENTS 0 185 465  11/1985  European Pat. Off. ........... C09J 3/14
0 311 715  10/1987  European Pat. Off. ...... C08F 220/18
0 383 497  2/1989  European Pat. Off. ....... C09J 133/08
WO 91/12290  8/1991  WIPO .............................. C08K 5/41
WO 92/01761  2/1992  WIPO ............................ C09J 133/08

Primary Examiner—Peter A. Szekely
Attorney, Agent, or Firm—Darby & Darby

[57] ABSTRACT

The invention provides a water-based adhesive composition comprising a blend of adhesive polymers in an aqueous system, characterized in that the blend of adhesive polymers is: 20–60% by weight of an acrylic polymer having a polarity balance expressed as water absorption according to DIN 53495 of 3 to 20%; and correspondingly 40–80% by weight of a compatible tackifying resin having a degree of hydrophobicity measured as the contact angle between a dried film of the resin and a drop of distilled water of not less than 60°; the percentages being based on the total of acrylic polymer plus tackifying resin expressed as dry solids. The composition shows good bond retention when wet and can be used for bonding polar substrates such as cellulose and non-polar substrates such as polyolefin. When used to bond a water absorbing substrate such as cellulose, the adhesive should have a viscosity of 200 mPas or less. The adhesive is particularly suitable for use in the manufacture of absorbent pads such as diapers and sanitary napkins.

20 Claims, No Drawings

WATER-BASED ADHESIVE COMPOSITION WITH BOND RETENTION IN THE PRESENCE OF WATER

This invention relates to a water-based adhesive composition which is suitable for bonding polar and non-polar substrates and which shows good bond retention in the presence of water. The adhesive composition is particularly suitable for use in the manufacture of absorbent pads, in particular diapers and sanitary napkins.

Water-based adhesives are known to have a number of advantages over solvent based and hot melt adhesives, in particular the following:

- water-based adhesives present less environmental problems;
- water-based adhesives have lower energy requirements in terms of their application and can be applied at room temperature;
- water-based adhesives can be formulated at low viscosity but high solids content even in the case of high molecular weight polymers.

In the bonding of two dissimilar materials, the more diverse the chemical nature of the materials to be bonded, the more difficult they are to bond. One example of the need to bond two materials which differ chemically is in the manufacture of absorbent pads, in particular diapers and sanitary napkins, in which it is necessary to bond a polar material such as cellulose to a non-polar material such as a polyolefin, e.g. polypropylene or polyethylene. Many adhesives are suitable for bonding either polar or non-polar materials but not the one to the other.

In many cases, particularly in the case of absorbent pads, it is necessary that the bond retain its strength when wet and retention of a substantial fraction of the bond strength is desirable even after contact with water for several hours at body temperature. At present, the manufacture of absorbent pads often uses hot melt adhesives and although these form a true adhesive bond with non-polar substrates such as polyolefin, they probably form only a mechanical bond with cellulose by interlocking with the cellulose fibres. As a result the bond formed by hot melt adhesives between polyolefin and cellulose is relatively easy to debond when wet.

Some water based adhesives are known to be capable of adhering to a wide variety of substrates, both polar and non-polar, provided that the adhesive itself has the correct balance of polar and non-polar characteristics. Known adhesives of this sort include:

- vinylic emulsions, especially those based on vinyl acetate or other vinyl esters and ranging from homopolymers to copolymers with ethylene and/or acrylic monomers (vinyl acrylics). In all vinylic emulsions vinyl esters, and especially vinyl acetate, are the major component.
- acrylic emulsions which may be either homopolymers or copolymers.

The polar character of acrylics is generally much higher than vinylics so that whilst adhesion to polar substrates (such as cellulose) is good, adhesion to non-polar substrates such as polyolefins can be unsatisfactory.

Water resistance of the bond formed by water based adhesives is typically poor, particularly in the case of vinylics. Water resistance is generally measured as percent bond retention after immersion in water at room temperature for a standard time, e.g. 1 hour. Water resistance ranges from zero (quick, self-debonding of the sample after a short immersion period) to values of 10 or 15% which have, in the past, been regarded as satisfactory.

The manufacture of absorbent pads requires that a non-polar substrate such as polyolefin be bonded to a polar substrate such as cellulose using an adhesive capable of providing a bond with high water resistance, e.g. bond retention of at least 30% of the dry value even after several hours immersion in water at body temperature. It has generally been thought that bond retention at this sort of level when wet can only be achieved with a water-borne adhesive by cross-linking of the adhesive. Cross-linking is generally achieved by including a reactive co-monomer (e.g. a monomer containing carboxyl, hydroxyl, epoxy, amide, isocyanate or the like functionality), which reactive co-monomers are capable of cross-linking the polymer themselves (e.g. carboxyl groups reacting with hydroxyl, epoxy or isocyanate groups) or by reaction with an external cross-linker (e.g. urea-formaldehyde resin, isocyanates, polyols, epoxides, amines and metal salts, especially zinc).

Many of these cross-linking systems are unsuitable for use in products in the hygiene field for toxicological reasons, for example products which might contain unreacted active monomers or zinc or other metals cannot be used safely in contact with the human skin. Furthermore, cross-linking often requires a treatment at elevated temperature which involves increased energy consumption and lower speed in production lines.

Modification has been proposed of both vinylic and acrylic emulsions for various purposes. Vinylics in particular may contain polyvinyl alcohol as emulsion stabiliser but this makes the bond particularly water sensitive and emulsion stabilisation by a surfactant is to be preferred. It is necessary in the formulation of some water based adhesives, for example those based on natural rubber latexes, to add tackifying resins in order to improve the tack of the adhesive. Vinylic and acrylic resins generally show good adhesion in unmodified form so that addition of tackifying resins is unnecessary. However, addition of limited quantities of compatible resins to both vinylics and acrylics has been suggested either with a view to reducing cost or improving adhesion in special applications.

Thus, the addition of limited quantities of tackifying resin to vinylics and acrylics has been suggested for the purpose of improving adhesion to non-polar substrates such polyolefins. For example, technical literature from the company Hercules recommends addition of the Hercules product HERCOLYN D (a hydrogenated rosin ester) at a level of about 5% by weight to the Air Products, Inc. vinylic emulsion AIRFLEX 400 (vinyl acetate/ethylene copolymer latex) for the bonding of paper to polypropylene film. Suppliers of acrylic adhesives (such as BASF) or resins (such as Hercules) state in their technical literature that the usual level of modification of acrylics with resin where this is considered to be desirable is about 10–20% resin. Hercules suggest that higher levels of tackifying resin of up to 35 to 45% can be added for some applications.

EPA 0 508 400 describes pressure sensitive adhesives comprising tackified aqueous vinyl acetate/ethylene/acrylate copolymer dispersions. The composition comprises the tackified resin in an amount of 5 to 60 wt %, on a total solids basis.

The copolymer consists essentially of 5 to 40 wt % vinyl acetate, 5 to 30 wt % ethylene and 20 to 90 wt % acrylate monomer.

There is no reference in EPA 0 508 400 to the water absorption characteristics of the copolymer and the vinyl acetate content of the copolymer (preferably 10 to 25 wt %) would lead to increased water sensitivity which is in contrast to the definition of the present invention where a degree of hydrophobicity is required.

An object of the present invention is to provide a water based adhesive which produces a bond between substrates showing a high bond retention, preferably at least 30% of the dry value, when wet, for example following immersion in water at body temperature for 1 hour, more preferably for 8 hours. Preferably the adhesive shows good adhesion to both polar substrates (e.g. cellulose) and non-polar substrates (e.g. polyolefin) so that it is particularly suitable for use in the manufacture of absorbent pads such as diapers and sanitary napkins.

According to the present invention, it has been found that water-based adhesives can be produced which provide a bond showing good water resistance by adding levels of compatible tackifying resin to acrylic polymer emulsions at a level which is higher than previously suggested for general use and which may even be such that the tackifying resin is the major adhesive component in the system. Provided that the acrylic polymer has the correct balance of polar and non-polar groups and the tackifying resin has an appropriate degree of hydrophobicity, the adhesive shows good adhesion to both polar and non-polar materials and provides an adhesive bond showing good or even outstanding resistance to water.

The present invention provides a water based adhesive composition comprising a blend of adhesive components in an aqueous system, characterised in that the blend of adhesive components is:

20–60% by weight of an acrylic polymer having a polarity balance expressed as water absorption according to DIN 53495 of 3 to 20%; and correspondingly 40–80% by weight of a compatible tackifying resin having a degree of hydrophobicity measured as the contact angle between a dried film of the resin and a drop of distilled water of not less than 60°;

the percentages being based on the total of acrylic polymer plus tackifying resin expressed as dry solids.

According to another aspect, the present invention provides the use of a tackifying resin having a degree of hydrophobicity measured as the contact angle between a dried film of the resin and a drop of distilled water of not less than 60° for improving the water resistance of the bond of a water based adhesive composition based on a compatible acrylic polymer having a polarity balance expressed as water absorption according to DIN 53495 of 3 to 20%, by formulating an aqueous dispersion of the acrylic polymer with the tackifying resin in an amount of 20 to 60% of acrylic polymer to correspondingly 40 to 80% tackifying resin, the percentages being based on the total of acrylic polymer and tackifying resin expressed as dry solids.

The water based adhesive composition referred to above can be used for bonding polar substrates or non-polar substrates and is also particularly suitable for use in the bonding of a polar substrate such as cellulose to a non-polar substrate such as a polyolefin. However, when the polar substrate is a water absorbing material (as with cellulose), it is important that the water based adhesive have a low viscosity, generally 200 cps (mPas) or less. In the case of adhesives with a high viscosity, it is generally sufficient to reduce the viscosity by dilution with water. In the case of the bonding of absorbent substrates such as cellulose, viscosity is important to the effectiveness of the adhesive and high viscosity weakens both the dry and especially the wet bond strength. However, on non-absorbent substrates, such as polyolefin non-wovens and polyolefin film, the viscosity of the adhesive does not generally have a significant effect on bond strength either in dry or wet conditions.

The present invention also provides a method of bonding two substrates characterised by the use of a water based adhesive as defined above as bonding agent. According to one embodiment of this method, both substrates are non-absorbent to water, for example the bonding of two polyolefin substrates such as the bonding of a polyolefin film to a polyolefin non-woven or the bonding of two polyolefin films at least one of which is perforated. According to another embodiment of the method, at least one of the substrates is water absorbent, for example the bonding of cellulose, such as a cellulosic non-woven, to a polyolefin, such as a polyethylene film, in which case the water based adhesive has a low viscosity, in general a viscosity of 200 cps (mPas) or less.

The water based adhesive composition according to the invention is based on a blend of two adhesive components (acrylic polymer and tackifying resin) and in the following description references to the percentage of a particular component are based on the total of the two components expressed as dry solids. The first component is from 20 to 60% by weight, preferably 30 to 50% by weight, of an acrylic polymer or copolymer or a blend of such polymers or copolymers. Suitable acrylic polymers are generally produced as a latex or emulsion and are homopolymers or copolymers having a balance of polar and non-polar characteristics making them suitable for bonding both polar and non-polar substrates. Preferably this balance is achieved by the use of copolymers which are formed from a mixture of polar acrylic monomers such as acrylic and methacrylic acid esters having a total of 4 to 20 carbon atoms; acrylic and methacrylic acids, acrylamide, methacrylamide and acrylonitrile, and non-polar monomers such as hydrocarbon monomers, especially styrene. Vinyl monomers such as vinyl esters, especially vinyl acetate may be useful co-monomers from the point of view of the adhesive properties of the composition but they increase the water sensitivity of the polymer and preferably should not be used in an amount of more than 10% by weight.

The balance of polar and non-polar character in the acrylic polymer, which is necessary to ensure that the adhesive will bond to a range of different substrates is best characterised by its water absorption and water absorption may, in turn, be judged by the standard method according to DIN 53495 which gives a value for percentage weight increase of a dried polymer after immersion in water for 24 hours at room temperature. A non-polar polymer will give a value for weight increase of close to zero, whereas a highly polar acrylic polymer will often show a weight increase of 50% or even higher (say 70%). The optimum balance of adhesive properties is achieved with an acrylic polymer with a water absorption according to DIN 53495 of 3 to 20%, preferably from 5 to 15%, which provides not only a balanced polarity but also shows that the polymer is not too sensitive to water.

The second component is from 40 to 80%, preferably from 50 to 70%, by weight of a tackifying resin or a blend of such resins. The tackifying resin must be compatible with the acrylic polymer in the sense that the two components are mutually soluble. Compatibility is generally indicated by a blend of the two components forming a clear film. The tackifying resin is also preferably used as a water based emulsion.

Suitable tackifying resins include rosin and rosin derivatives; terpene resins; hydrocarbon resins; phenolic and terpene-phenolic resins; and aromatic resins. In order to confer water-resistance on the bond produced by the adhesive composition, the tackifying resin must be sufficiently hydrophobic as judged by measuring the contact angle between a dried film of the resin and a drop of distilled water. In particular, to produce a bond with a suitable level of water resistance, the contact angle between the dried film of the tackifying resin and a drop of distilled water should be not less than 60°.

The hydrophobicity of the tackifying resin is determined not only by the chemical nature of the resin but also by the presence and quantity of certain additives, such as surfactants, in the resin emulsion. Tackifying resins may have the required degree of hydrophobicity as obtained from the manufacturer, for example the resin AQUATAC 6085 (aqueous dispersion of rosin ester produced by Arizona Co.). Alternatively, a suitable tackifying resin can be formulated as an aqueous dispersion with the degree of hydrophobicity required for use according to the present invention by use of an appropriate level of a suitable surfactant.

According to a preferred embodiment of the invention, the tackifying resin contains a balance of polar and non-polar groups as in the case of rosin esters which may optionally be hydrogenated. More preferably the tackifying resin is an optionally hydrogenated rosin ester or a mixture of such esters having a ring and ball (R&B) softening point of from 40 to 110° C.

The water based adhesive compositions according to the invention may contain other additives, such as those already known for water based adhesives, for example, plasticizers, pigments or fillers, thickeners, defoamers, biocides, UV-protectors and surfactants.

The addition of one or more plasticizers may enhance both adhesion and water resistance and plasticizers may be present, for example, in an amount of up to 20 parts by weight based on 100 parts by weight of the blend of acrylic polymer and tackifying resin expressed as dry solids. Examples of plasticizers include phthalates, liquid resins such as hydrogenated rosin esters, for example the product HERCOLYN D of Hercules, and polypropylene glycol alkylphenyl ethers, for example the product PLASTILIT 3060 of BASF. Although certain plasticizers are similar in terms of chemical nature to the tackifying resin, for example both may be hydrogenated rosin esters, they are distinguished in terms of properties and, in particular, the rheological properties that they produce in the blend. Both tackifying resins and plasticizers tend to lower the storage modulus of the overall blend (plasticizers more so than tackifying resin). However, tackifying resins produce an increase in the modulus with applied stress frequency whereas plasticizers do not produce any variation, or produce lower variation, of the modulus with applied stress frequency.

Pigments, such as titanium dioxide, and/or mineral fillers such as calcium carbonate, talc, silica and silicates, may also be added to the water based adhesive composition, generally in amounts of up to 50 parts by weight based on 100 parts by weight of the blend of acrylic polymer and tackifying resin.

Addition of one or more surfactants may assist in ensuring that the water based adhesive wets difficult surfaces such as polyolefins. However, in order not to compromise water resistance, the amount of surfactant should generally not exceed 3 parts per 100 parts of the blend of acrylic polymer and tackifying resin.

The water based adhesive according to the invention is particularly suitable for use in the manufacture of products where it is necessary to bond a polar substrate, such as a cellulose based substrate, to a non-polar substrate, such as a polyolefin film, e.g. polyethylene film, and where retention of the bond strength is necessary after wetting with water. One such application is in the manufacture of absorbent pads, for example diapers, incontinence products and sanitary napkins. The water based adhesive compositions are also suitable for bonding two non-polar substrates, for example bonding a polyolefin film to a polyolefin non-woven or bonding two polyolefin films at least one of which is perforated, and this may also be applicable in the manufacture of absorbent pads. In any event, in all applications of water based adhesives, provision must be made for the evaporation of the water, generally by at least one of the substrates being perforated or otherwise permeable to water vapour.

The invention is illustrated by the following non-limiting examples. In all cases (except Example 6) bond strengths were measured by using the product in question at a solid level of 11 to 14 g/m$^2$ dry solids to bond a non-polar substrate, constituted by a polyethylene film with a basis weight of 24 g/m$^2$ and a thickness of 25$\mu$, to a polar substrate constituted by a spun laced cellulose (rayon) non-woven with a basis weight of 50 g/m$^2$ and a thickness of 550$\mu$. Example 6 uses the composition to bond different substrates but at a similar solids level. The substrates are constituted by the same polyethylene film used in the other examples and by a polypropylene non-woven in the form of a perforated fiber/film composite commonly used as a covering structure for sanitary products and as described in EP-A-0207 904, having an overall thickness of 470$\mu$, a basis weight of 40 g/m$^2$ and an open area of 24% with square 0.5 mm$^2$ holes.

The bond strengths have been measured according to the partially modified ASTM D 1876-72 (1983) (T-PEEL TEST) standard method: the head speed of the testing machine is 100 mm/min and each value is achieved as a mean from three tests. The specimens are obtained from a laminated panel of standard dimensions which is prepared by uniformly distributing the desired amount of adhesive on the polyolefin film by means of a Mayer bar, and then making the fibrous substrate (polypropylene non-woven comprised in the perforated fiber/film composite for Example 6 only and spun laced cellulose (rayon) non-woven for all other cases) adhere on it. The laminated panel is left for 24 hours at 23° C. and at a relative humidity of 50 percent under a pressure of 0.39 kPa and is subsequently cut in order to form the specimens of standard dimensions. The dry bond strength is evaluated testing the specimens in dry condition; for the wet bond strength the specimens are previously put in distilled water at the temperature of 37° C. for the desired time; they are subsequently taken out of water and laid down on a tissue layer in order to absorb the excess water and immediately after they are tested on the testing machine.

EXAMPLE 1

Comparative

A vinylic emulsion stabilised with surfactants and polyvinyl alcohol, was used as adhesive. The specific material was MOWILITH DM 132 (emulsion of vinyl acetate/ethylene copolymer) which is a product of Hoechst. The product has a solids content of 60% by weight and a viscosity of 2450 cps (mPas) but for use in this test it was diluted with 30% water to a final viscosity of 32 cps (mPas).

Use as described above gave a dry bond strength of 0.94 N/cm whereas after 30 minutes in water at 37° C. the bond strength was 0.20 N/cm showing that the water resistance of the bond was unsatisfactory.

EXAMPLE 2

Comparative

Another vinylic emulsion was used as adhesive, the specific material being VINNAPAS EVA 491-R (emulsion of a copolymer of vinyl acetate and ethylene) which is a product of Wacker-Chemie. The product has a solids content of 55% and a viscosity of 128 cps (mPas) and does not contain polyvinyl alcohol so that water resistance of the bond would be expected to be good.

Use as described above gave a dry bond strength of 2.28 N/cm whereas after 30 minutes in water at 37° C. the bond strength was 0.08 N/cm showing that the water resistance of the bond was unsatisfactory.

EXAMPLE 3

Comparative

This example illustrates the use of an acrylic polymer emulsion without addition of a tackifying resin as an adhesive. The acrylic polymer emulsion was ACRONAL DS 3434 (aqueous emulsion of an acrylic copolymer based on methyl methacrylate, methyl acrylate and styrene) which is a product of BASF. The product has a solids content of 60%, a viscosity of 100 cps (mPas) and the water absorption according to DIN 53495 is 10% in 24 hours.

Use as described above gave a dry bond strength of 1.06 N/cm whereas after 30 minutes in water at 37° C. the bond strength was 0.06 N/cm showing that the water resistance of the bond was unsatisfactory.

EXAMPLE 4

A) The polymer described in Example 3 (ACRONAL DS 3434) was modified by addition of a tackifying resin. The resin was AQUATAC 6085 (aqueous dispersion of a rosin ester) which is a product of Arizona Co and has the following characteristics:

solids content—60%;

softening point (R&B) of the base resin—83° C.;

contact angle of the dry film with a drop of distilled water—62°.

The adhesive had the composition:

AQUATAC 6085 60% by weight

ACRONAL DS 3434 40% by weight (percentages being based on the total of the two components expressed as dry solids) and the composition had a viscosity of 315 cps (mPas).

Use as described above gave a dry bond strength of 1.26 N/cm whereas after 30 minutes in water at 37° C. the bond strength was 0.16 N/cm showing that the water resistance of the bond was unsatisfactory.

B) The adhesive described in Part A above was diluted with 10% water to a final viscosity of 155 cps (mPas). Use as described above gave a dry bond strength of 2.24 N/cm whereas after 8 hours in water at 37° C. the bond strength was 1.02 N/cm; a bond retention of well over 30% even after 8 hours in water.

Parts A and B of this example involve the use of the same adhesive polymers but the difference is the viscosity and these examples illustrate the fact that a low viscosity of about 200 cps (mPas) or less is required for satisfactory bond strength when one of the substrates to be bonded is a water absorbent material such as cellulose.

EXAMPLE 5

The same adhesive as described in Example 4 was used to bond two non-absorbent substrates, constituted as previously described by a polyethylene film and a polypropylene non-woven in the form of a perforated fiber/film composite. The substrates were the same polyethylene film used in previous examples and a polypropylene non-woven in the form of a perforated fibre/film composite commonly used as a covering structure for sanitary products and as described in EP-A-0 207 904. The results were as follows:

AQUATAC 6085—60% by weight/ACRONAL DS 3434—40% by weight i) undiluted—viscosity 315 cps (mPas) dry bond strength—1.06 N/cm bond strength after 8 hours in water at 37° C.—0.67 N/cm;

ii) diluted 90:10—viscosity 155 cps (mPas) dry bond strength—1.00 N/cm bond strength after 8 hours in water at 37° C.—0.59 N/cm.

These results show that viscosity does not have a significant effect on the water resistance of the bond and in both cases the bond retention was around 60% even after 8 hours in water.

EXAMPLE 6

A different acrylic polymer was formulated in the same manner as described in Example 4. The acrylic polymer was ACRONAL V205 (emulsion of an acrylic copolymer based on methyl methacrylate, styrene and vinyl acetate but said to contain less than 10% vinyl acetate) which is a product of BASF. The product has a solids content of 69% and the water absorption according to DIN 53495 is 10% in 24 hours.

A mixture of:

AQUATAC 6085 60% by weight

ACRONAL V205 40% by weight (percentages being based on the total of the two components expressed as emulsions) gave a viscosity of 1150 cps (mPas) but when diluted with 20% water gave a viscosity of 50 cps (mPas).

When used in diluted form to bond polyethylene film to spun laced cellulosic non-woven as described above, the product gave a dry bond strength of 2.05 N/cm whereas after 8 hours in water at 37° C. the bond strength was 0.98 N/cm; a bond retention of about 48% even after 8 hours in water.

EXAMPLE 7

A third acrylic polymer was formulated in the same manner as described in Example 4. The acrylic polymer was REVACRYL 123 (acrylic polymer emulsion having a solids content of 60% and said to be a copolymer of butyl acrylate, styrene and acrylonitrile) which is available from Harlow Chemical Co. The product has a water absorption according to DIN 53495 of less than 10% in 24 hours.

A mixture of:

AQUATAC 6085 60% by weight

REVACRYL 123 40% by weight gave a viscosity of 810 cps (mPas) but when diluted with 10% water gave a viscosity of 75 cps (mPas).

When used in diluted form to bond polyethylene film to spun laced cellulosic non-woven as described above, the product gave a dry bond strength of 2.13 N/cm whereas after 8 hours in water at 37° C. the bond strength was 1.22 N/cm; a bond retention of about 57% even after 8 hours in water.

EXAMPLE 8

The same blend of adhesive polymers as described in Example 6 was formulated with a higher proportion of resin as follows:

AQUATAC 6085 70% by weight

ACRONAL V205 30% by weight (percentages being based on the total of the two components expressed as emulsions) to give a composition with a viscosity of 415 cps (mPas) which was diluted with 10% water gave a viscosity of 120 cps (mPas).

When used in diluted form to bond polyethylene film to spun laced cellulosic non-woven as described above, the product gave a dry bond strength of 1.97 N/cm whereas after 8 hours in water at 37° C. the bond strength was 0.79 N/cm; a bond retention of 40% even after 8 hours in water.

EXAMPLE 9

Comparative

The same blend of adhesive polymer and tackifying resin as described in Example 4 was formulated but with the addition of the amount of tackifying resin to acrylic polymer suggested by the prior art for modification of acrylics so as to maximise adhesion to a range of different materials including polyolefins as follows:

ACRONAL DS 3434 80% by weight
AQUATAC 6085 20% by weight to give a viscosity of 130 cps (mPas).

Use of this composition to bond polyethylene film to spun laced cellulosic non-woven as described above gave a dry bond strength of 1.77 N/cm whereas after 30 minutes in water at 37° C. the bond strength was 0.31 N/cm. This shows that proportions of acrylic polymer to tackifying resin outside the range prescribed according to the invention led to unsatisfactory water resistance of the bond.

EXAMPLE 10

Comparative

An acrylic polymer not meeting the requirements for use according to the present invention was used in place of ACRONAL DS 3434 in a composition similar to that of Example 4. The acrylic polymer was ACRONAL V302 (an emulsion copolymer based on butyl acrylate and vinyl acetate) available from BASF. The product has a solids content of 55% and a water absorption according to DIN 53495 of 30% in 24 hours. The composition:

AQUATAC 6085 60% by weight
ACRONAL V302 40% by weight (percentages being based on the total of the two components expressed as emulsions) gave a viscosity of 275 cps (mPas) and was diluted 10% with water to give a final viscosity of 85 cps (mPas).

Use of this composition to bond polyethylene film to spun laced cellulosic non-woven as described above gave a dry bond strength of 2.32 N/cm whereas after 30 minutes in water at 37° C. the bond strength was 0.24 N/cm. This shows that use of an acrylic polymer with a water absorption according to DIN 53495 outside the range required by the present invention (i.e. lacking the required balanced polarity), led to unsatisfactory water resistance of the bond.

EXAMPLE 11

Comparative

The vinylic copolymer described in Example 2 was formulated with a tackifying resin as follows:

AQUATAC 6085 60% by weight
VINNAPAS EVA 491-R 40% by weight (percentages being based on the total of the two components expressed as emulsions) to give a composition with a viscosity of 215 cps (mPas) which was diluted 10% with water to give a final viscosity of 90 cps (mPas).

Use of this composition to bond polyethylene film to spun laced cellulosic non-woven as described above gave a dry bond strength of 1.81 N/cm whereas after 30 minutes in water at 37° C. the bond strength was 0.08 N/cm. This shows that a blend of a vinylic copolymer and a tackifying resin did not lead to satisfactory water resistance of the bond.

EXAMPLE 12

Comparative

A tackifying resin not meeting the requirements for use according to the present invention was used in place of AQUATAC 6085 in a composition similar to that of Example 6. The tackifying resin was HERCULES MBG 170 (an aqueous emulsion of a rosin derivative) available from Hercules and having the following characteristics:

solids content—55%;
softening point (R&B) of the base resin—65° C.;
contact angle of the dry film with a drop of distilled water—53°.

The composition:

HERCULES MBG 170 60% by weight
ACRONAL V205 40% by weight (percentages being based on the total of the two components expressed as emulsions) gave a viscosity of 180 cps (mPas).

Use of this composition to bond polyethylene film to spun laced cellulosic non-woven as described above gave a dry bond strength of 2.09 N/cm whereas after 30 minutes in water at 37° C. the bond strength was 0.16 N/cm. HERCULES MBG 170 is fully compatible with ACRONAL V205 and the composition referred to above dries to a completely clear film. According to the manufacture HERCULES MBG 170 has exceptional resistance to water but, as indicated by the contact angle with water, appears to be too hydrophilic for use according to the present invention.

EXAMPLE 13

Comparative

Another tackifying resin not meeting the requirements for use according to the present invention was used in place of AQUATAC 6085 in a composition similar to that of Example 7. The tackifying resin was TACOLYN 1100 (an aqueous emulsion of a hydrocarbon resin) available from Hercules and having the following characteristics:

solids content—55%;
softening point (R&B) of the base resin—100° C.;
contact angle of the dry film with a drop of distilled water—42°.

The composition:

TACOLYN 1100 60% by weight
REVACRYL 123 40% by weight (percentages being based on the total of the two components expressed as emulsions) gave a viscosity of 78 cps (mPas).

Use of this composition to bond polyethylene film to spun laced cellulosic non-woven as described above gave a dry bond strength of 1.93 N/cm whereas after 30 minutes in water at 37° C. the bond strength was 0.20 N/cm. TACOLYN 1100 is fully compatible with REVACRYL 123 but, as indicated by the contact angle with water, also appears to be insufficiently hydrophobic for use according to the present invention.

I claim:

1. A water-based adhesive composition comprising a blend of adhesive polymers in an aqueous system, which produces a bond between substrates with a bond retention of at least 30% of the dry value following immersion in water at body temperature for one hour, wherein the blend of adhesive polymers is:

20–60% by weight of an acrylic polymer having a polarity balance expressed as water absorption according to DIN 53495 of 3 to 20%, wherein said acrylic polymer contains not more than about 10% by weight of a vinyl monomer; and correspondingly 40–80% by weight of a compatible tackifying resin selected from the group consisting of hydrogenated rosins, terpene resins, phenolic resins, terpene-phenolic resins and mixtures thereof, having a degree of hydrophobicity measured as the contact angle between a dried film of the resin and a drop of distilled water of not less than 60°;

the percentages being based on the total of acrylic polymer plus tackifying resin expressed as dry solids.

2. An adhesive composition according to claim 1, having a viscosity of 200 mPas or less.

3. An adhesive composition according to claim 1 wherein the amount of acrylic polymer is 30 to 50% by weight.

4. An adhesive composition according to claim 1, wherein the acrylic polymer is a copolymer of at least one polar acrylic monomer and at least one non-polar monomer.

5. An adhesive composition according to claim 4, wherein the polar acrylic monomer is selected from the group consisting of acrylic acid esters having a total of 4 to 20 carbon atoms, methacrylic acid esters having a total of 4 to 20 carbon atoms, acrylic acid, methacrylic acid, acrylamide, methacrylamide and acrylonitrile.

6. An adhesive composition according to claim 4, wherein the non-polar monomer is a hydrocarbon monomer.

7. An adhesive composition according to claim 6, wherein the hydrocarbon monomer is styrene.

8. An adhesive composition according to claim 1, wherein the acrylic polymer has a water absorption according to DIN 53495 of 5 to 15%.

9. An adhesive composition according to claim 1, wherein the amount of tackifying resin is 50 to 70%.

10. An adhesive composition according to claim 1, wherein the tackifying resin is selected from the group consisting of rosin, terpene resins, hydrocarbon resins, phenolic resins, terpene-phenolic resins, and aromatic resins and mixtures thereof.

11. An adhesive composition according to claim 1, wherein the tackifying resin is an optionally hydrogenated rosin ester or a mixture thereof.

12. An adhesive composition according to claim 11, wherein the optionally hydrogenated rosin ester or mixture thereof has a ring and ball softening point of from 40 to 110° C.

13. An adhesive composition according to, claim 1 comprising, based on 100 parts by weight of the blend of acrylic polymer and tackifying resin expressed as dry solids:

up to 20 parts by weight of plasticizer;
   up to 50 parts by weight of pigment or mineral filler;
   up to 3 parts by weight of surfactant.

14. A method of bonding two substrates which are non-absorbent to water which comprises uniformly distributing to either or both of the surfaces of the substrates to be bonded the water based adhesive composition of claim 1 and making the two substrates adhere.

15. A method of bonding two substrates, at least one of which is absorbent to water, which comprises uniformly distributing to either or both of the surfaces of the substrates to be bonded the water based adhesive composition of claim 1 having a viscosity of 200 mPas or less and making the two substrates adhere.

16. A method according to claim 15, wherein the two substrates are cellulosic and polyolefin respectively.

17. A method for the manufacture of an absorbent pad in which at least one cellulosic material is bonded to at least one polyolefinic material, which comprises uniformly distributing to either or both of the surfaces of the materials to be bonded a water based adhesive composition as claimed in claim 1 having a viscosity of 200 mPas or less.

18. A method of improving the water resistance of the bond of a water based adhesive composition based on a compatible acrylic polymer having a polarity balance expressed as water absorption according to DIN 53495 of 3 to 20% using a tackifying resin having a degree of hydrophobicity measured as the contact angle between a dried file of the resin and a drop of distilled water of not less than 60° and formulating an aqueous dispersion of the acrylic polymer with the tackifying resin in an amount of 20 to 60% of acrylic polymer to correspondingly 40 to 80% tackifying resin, the percentages being based on the total of acrylic polymer and tackifying resin expressed as dry solids.

19. A composition of claim 1 wherein said tackifying resin is a rosin ester with a solid content of 60% and a softening point of 83° C.

20. A composition of claim 1, said composition further comprising a surfactant.

* * * * *